(12) United States Patent
Hammer et al.

(10) Patent No.: US 10,073,027 B2
(45) Date of Patent: Sep. 11, 2018

(54) DEVICE FOR MEASURING FRICTION ON A CYLINDER/PISTON ARRANGEMENT

(71) Applicant: AVL LIST GMBH, Graz (AT)

(72) Inventors: Michael Erich Hammer, Seiersberg (AT); Wolfgang Meldt, Kumberg (AT)

(73) Assignee: AVL List GmbH, Graz (AT)

( * ) Notice: Subject to any disclaimer, the term of this patent is extended or adjusted under 35 U.S.C. 154(b) by 56 days.

(21) Appl. No.: 15/023,239

(22) PCT Filed: Oct. 2, 2014

(86) PCT No.: PCT/EP2014/071138
§ 371 (c)(1),
(2) Date: Mar. 23, 2016

(87) PCT Pub. No.: WO2015/049330
PCT Pub. Date: Apr. 9, 2015

(65) Prior Publication Data
US 2016/0238515 A1    Aug. 18, 2016

(30) Foreign Application Priority Data
Oct. 4, 2013    (AT) .............................. A 50639/2013

(51) Int. Cl.
*F02F 1/00*    (2006.01)
*G01L 5/00*    (2006.01)
(Continued)

(52) U.S. Cl.
CPC ............. *G01N 19/02* (2013.01); *F02B 77/08* (2013.01); *F02F 1/004* (2013.01); *G01L 5/00* (2013.01);
(Continued)

(58) Field of Classification Search
CPC ......... G01L 5/00; G01M 15/02; G01M 15/04; G01M 15/042; G01N 19/02; F02F 1/00;
(Continued)

(56) References Cited

U.S. PATENT DOCUMENTS 4,466,399 A  *  8/1984  Hinz ................... F02B 23/0675
                                                         123/193.1
6,167,847 B1    1/2001  Ergezen et al.
(Continued)

FOREIGN PATENT DOCUMENTS

JP    2010243390    10/2010
WO    2005068814    7/2005
(Continued)

OTHER PUBLICATIONS

English Abstract of JP 2010243390.

*Primary Examiner* — Nguyen Ha
(74) *Attorney, Agent, or Firm* — Dykema Gossett PLLC

(57) ABSTRACT

The invention relates to a device (1) for measuring friction on a cylinder-piston arrangement, wherein a reciprocating piston (3) is arranged in a cylinder liner (2) of a liner unit (23), said cylinder liner being decoupled from a cylinder head (9), and the liner unit (23) is arranged in a liner carrier (8) which is connected to a sensor carrier and which has a rotationally symmetrical receiving region (13) for the cylinder liner (2), said receiving region being concentric to the cylinder axis (21), wherein preferably at least one cooling jacket (12) is assigned to the cylinder liner (2). In order to enable easy replacement of the cylinder liner (2) it is provided that the liner unit (23) is mounted in the liner carrier (8) via a tapered seat (14), wherein preferably at least one tapered inner jacket surface of the receiving region (13) forms a first seat surface (14*a*) and a tapered outer jacket surface (19*a*, 19*b*) of the liner unit (23) that is shaped in a manner reciprocal to the first seat surface (14*a*) forms a
(Continued)

second seat surface (14b) of the tapered seat (14) for receiving and centring the cylinder liner (2).

9 Claims, 2 Drawing Sheets

(51) Int. Cl.
*G01M 15/02* (2006.01)
*G01M 15/04* (2006.01)
*G01N 19/02* (2006.01)
*F02B 77/08* (2006.01)

(52) U.S. Cl.
CPC .......... *G01M 15/02* (2013.01); *G01M 15/042* (2013.01)

(58) Field of Classification Search
CPC ... F02F 1/004; F02F 1/16; F02B 77/00; F02B 77/08
See application file for complete search history.

(56) References Cited

U.S. PATENT DOCUMENTS

2010/0095838 A1　　4/2010　Hittle et al.
2014/0102401 A1*　4/2014　Issler ..................... F02F 1/004
　　　　　　　　　　　　　　　　　　　　　123/193.2

FOREIGN PATENT DOCUMENTS

WO　　　2012062725　　　5/2012
WO　　WO 2012062725 A1 *　5/2012　............... G01L 5/00

* cited by examiner

DEVICE FOR MEASURING FRICTION ON A CYLINDER/PISTON ARRANGEMENT

BACKGROUND OF THE INVENTION

Field of the Invention

The invention relates to a device for measuring friction on a cylinder-piston arrangement, wherein a reciprocating piston is arranged in a cylinder liner of a liner unit, the cylinder liner being decoupled from a cylinder head, and the liner unit is arranged in a liner carrier which is connected to a sensor carrier and which has a rotationally symmetrical receiving region for the cylinder liner, the receiving region being concentric to the cylinder axis, wherein preferably at least one cooling jacket is assigned to the cylinder liner.

The Prior Art

The friction between a piston group which consists of a piston and piston rings and a cylinder liner surface can be determined from the integration of the forces along the piston bearing surface in the direction of the cylinder.

A device for measuring the friction in a cylinder-piston arrangement is known from WO 2012/062725 A1, wherein an inner jacket surface of the cylinder liner is sealed in relation to a cylinder head, in that a sealing element is arranged between the inner jacket surface and a shoulder of the cylinder head which protrudes into the cylinder liner.

A similar device is disclosed in JP 2010-243390 A.

A measuring device for measuring the friction of a piston reciprocating in a cylinder liner is known from JP 60-031037 A. A retaining ring is arranged between the cylinder head and a liner carrier, wherein an annular gap is formed between the retaining ring and the upper end of the cylinder liner, which is filled by a metallic sealing plate.

A device for measuring the piston friction in an internal combustion engine is known from JP 59-088638 A, wherein the cylinder liner is arranged in a cylinder and wherein several O-rings are arranged between the cylinder and the cylinder liner.

In order to enable the testing of different cylinder liners, it is necessary to frequently exchange the cylinder liners in the aforementioned devices for measuring the friction.

Known devices for measuring the friction come with the disadvantage that the liner carrier needs to be separated from the force sensor when exchanging the cylinder liner. This requires a new calibration of the sensor system in each exchange of the cylinder liners. Furthermore, the coolant supply needs to be made leakage-free with much effort in each exchange of the cylinder liner.

It is the object of the invention to avoid these disadvantages and to enable a simple exchange of the cylinder liner.

SUMMARY OF THE INVENTION

This is achieved in accordance with the invention in such a way that the liner unit is mounted in the liner carrier via a tapered seat, wherein preferably at least one tapered inner jacket surface of the receiving region forms a first seat surface and a tapered outer jacket surface of the liner unit that is shaped in a manner reciprocal to the first seat surface forms a second seat surface of the tapered seat for receiving and centering, the cylinder liner.

The liner unit which comprises the cylinder liner can thus be inserted in a very simple manner into the liner carrier and can be removed therefrom again without having to dismount liner carrier. An exchange of the cylinder liner can thus occur without having to carry out a new calibration of the sensor system (force sensors). The tapered seat allows simple self-centering of the cylinder liner in the liner carrier transversely to the cylinder axis and ensures a positionally correct installation of the cylinder liner.

The liner carrier can accommodate the cylinder liner directly or indirectly. It is provided in an embodiment with indirect accommodation that the liner unit comprises a liner frame, wherein the cylinder liner is arranged in the liner frame, and wherein the cylinder liner and the liner frame can rigidly be connected to each other, especially in a non-detachable and destruction-free manner. The liner frame can form the second seat surface. It is especially advantageous if the at least one coolant jacket is formed between the liner frame, which is preferably substantially formed in the manner of a sleeve, and an outer jacket surface of the cylinder liner. In order to achieve the freedom from leakages in the simplest possible way, the cylinder liner and liner frame can be connected to each other by pressing and/or casting. This allows a liquid-tight connection between the cylinder liner and liner frame without requiring any further sealing elements.

The coolant jacket can be arranged at least partly on the outer circumference of the cylinder liner and/or on the inner circumference of the liner frame, or it can be moulded therein.

The first seat surface preferably has an opening angle in relation to the cylinder axis of the cylinder liner which opens in the direction of the cylinder head and which is preferably between 5° and 15°, more preferably around 10°.

If the cylinder liner is accommodated indirectly by the liner carrier, the liner frame is situated between the liner carrier and the cylinder liner. The tapered seat is thus formed by the liner carrier and the liner frame. A tapered outer jacket surface of the liner frame that is shaped in a manner reciprocal to the first seat surface forms a second seat surface of the tapered seat in this case.

If on the other hand the cylinder liner is accommodated directly by the liner carrier, the tapered seat is formed by the liner carrier and the cylinder liner itself. A tapered outer jacket surface of the liner frame that is shaped in a manner reciprocal to the first seat surface, preferably a liner flange of the cylinder liner, forms the second seat surface of the tapered seat in this case.

The cylinder liner and/or the liner frame can be fastened via a retaining ring on the liner carrier.

BRIEF DESCRIPTION OF THE DRAWINGS

The invention will be explained below in greater detail by reference to non-limiting embodiments shown in the drawings, wherein.

DETAILED DESCRIPTION OF THE DEPICTED EMBODIMENTS

Figure 1:
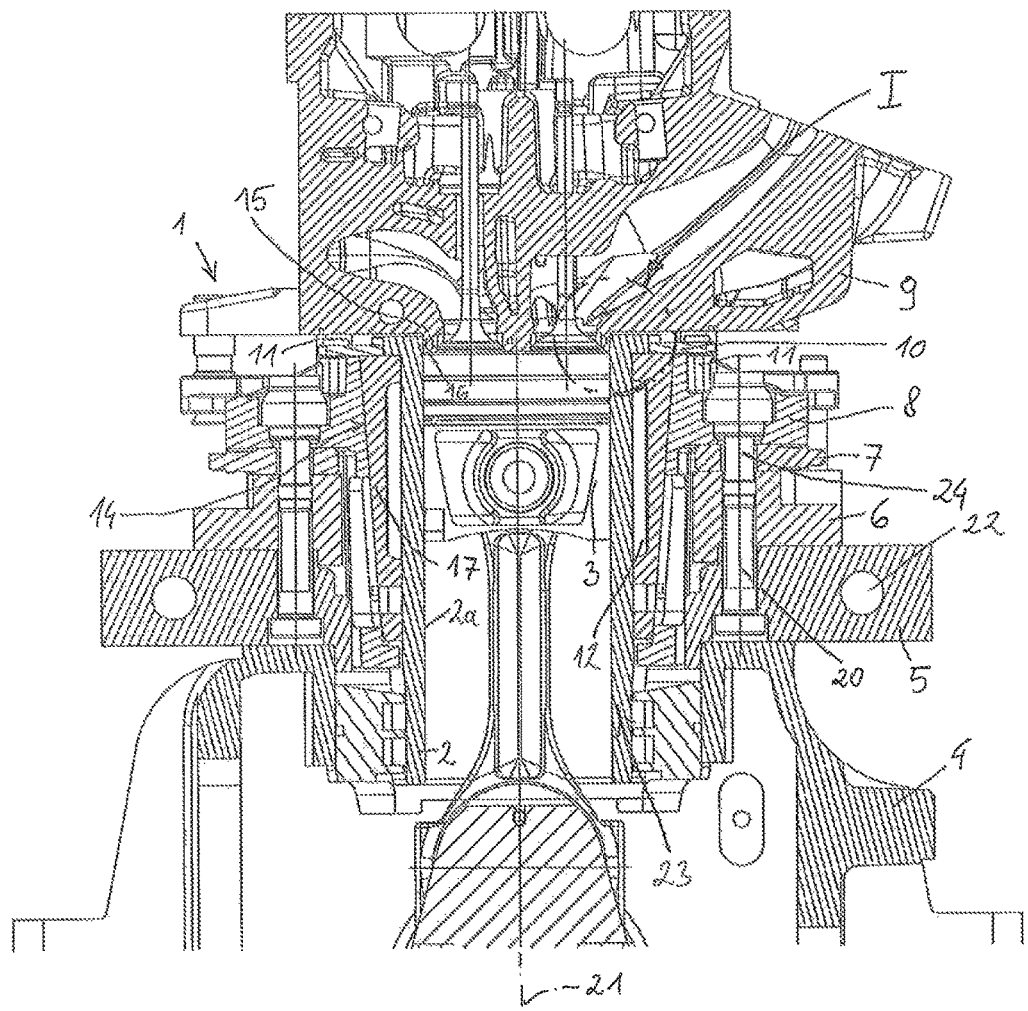
FIG. 1 shows a device in accordance with the invention in a longitudinal sectional view in a plane containing the cylinder axis, in a first embodiment.

Functionally identical parts are provided in the following embodiments with the same reference numerals.

The device 1 shown in FIG. 1 for measuring the friction of the frictional forces between a piston 3 reciprocating in a cylinder liner 2 of a liner unit 23 comprises a basic unit 4, a base plate 5, a sensor carrier 6 for accommodating 3D force sensors 7, a liner carrier 8 and a cylinder head 9. The base plate 5 is fastened to the bask unit 4 via screws (not shown in closer detail). The cylinder liner 2 is fastened via a retaining ring 10 to the liner carrier 8, wherein the retaining ring 10 is screwed by means of screws 11 to the liner carrier 8. The liner carrier 8 is rigidly connected via force sensors 7 by retaining screws 24 to the sensor carrier 6 and further via screws 20 to the base plate 5. A coolant jacket 12 is formed in the region between the cylinder liner 2 and the liner carrier 8, which cooling jacket is connected to feed and discharge lines which are not shown in closer detail. The liner unit 23 comprises the cylinder liner 2 forming the cylinder for the piston 3 plus the liner flange 18, the coolant jacket 12 and a liner frame 17 accommodating the cylinder liner 2, in the embodiment shown in FIG. 1 and FIG. 2.

Figure 1A:
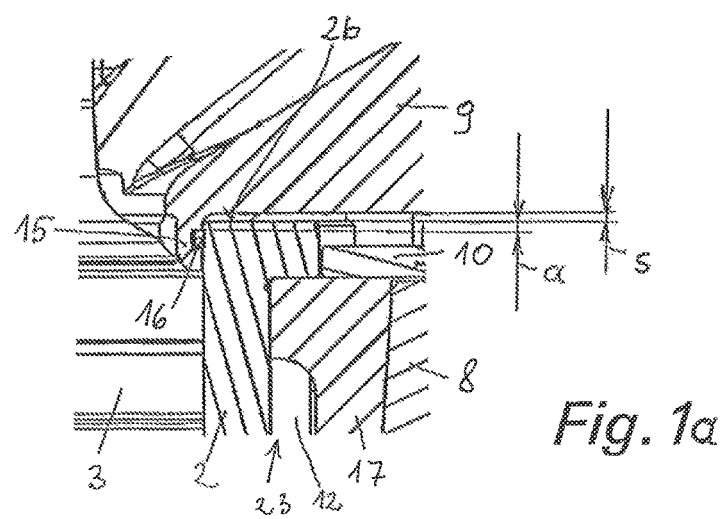
FIG. 1a shows the detail I of FIG. 1.

As is shown in FIG. 1, the cylinder head 9 comprises a disc-shaped shoulder 15 which protrudes into the cylinder liner 2 and in the outer jacket surface of which an annular groove is arranged for accommodating an annular sealing element 16, which similar to a piston ring is pressed by gas forces against the inner jacket surface 2a of the cylinder liner 2. An axial distance a is provided between the sealing element 16 and the upper edge 2b of the cylinder liner 2, in which production tolerances of the cylinder liner 2 and the cylinder head 9 are taken into account (FIG. 1a).

As a result of the special sealing by means of the annular sealing element 16 and the shoulder 15 in the cylinder head 9 it is prevented that the gas forces act axially on the cylinder liner 2. Consequently, they also have no direct influence on the results of the measurement and the frictional forces of the piston 3 or the lateral piston forces are mainly transferred to the force sensors 7. The cylinder liner 2 is thus substantially decoupled from the basic unit 4 and the cylinder head 9, and is only connected thereto by the sealing element 16 and the force sensors 7.

In order to reduce the forces acting normally to the running direction of the piston on the force sensors 7 during the measuring operation of the engine, which forces do not originate from the movement of the piston 3 (forces as a result of different thermal expansions) and which thus may falsify the results of the measurement, it needs to be ensured that prior to the start of the measurements the parts acting on the force sensor 7 (liner carrier 8, sensor carrier 6) have similar temperatures. Similar thermal expansions of these parts can thus be realised and the influence of the thus occurring transverse forces on the force sensors 7 can thus be reduced.

For this purpose, the base plate 5 is provided with conditioning channels 22 with an inlet and an outlet (not shown) for cooling liquid in order to bring the base plate 5 and therefore the sensor carrier 6 that is screwed onto said plate and the liner carrier 8 arranged in the same coolant circuit to the same temperature.

The liner carrier 8 comprises a rotationally symmetrical receiving region 13 for the cylinder liner 2. The inner diameter D of the receiving region 13 is greater in at least one first section 13a close to the cylinder head than the inner diameter d of the receiving region 13 in a second section 13b which is remote from the cylinder head.

In particular, the receiving region 13 can be formed in a tapered way, wherein a tapered inner jacket surface of the receiving region 13 forms a first seat surface 14a of a tapered seat 14 for accommodating the cylinder liner 2. A tapered outer jacket surface of the cylinder liner 2 which is shaped in a manner that is reciprocal to the first seat surface 14a, especially a liner flange 18 of the cylinder liner 2 (FIGS. 3 to 5) or the liner frame 17 (FIG. 2), forms a second seat surface 14b of the tapered seat 14.

The tapered first and second seat surfaces 14a, 14b each have an opening angle a with respect to the cylinder axis 21 which opens in the direction of the cylinder head 9.

A gap s is necessary in the axial direction between the cylinder liner 2 and the cylinder head 9, which gap is produced by production tolerances of the liner unit 23, especially the cylinder liner 2 and the liner carrier 8. The selection of the opening angle a therefore depends on the radial production tolerances of the liner unit 23 on the one hand, especially the cylinder liner 2 and the liner frame 17, as well as the liner carrier 8, and the thus occurring axial displacements of the liner unit 23.

The following is obtained for the opening angle a with the maximum possible radial deviation $\varepsilon_L$ of the liner unit 21 caused by production and the maximum possible radial deviation $\varepsilon_C$ of the liner frame 17 from the design specification:

$$\alpha > \arctan\left(\frac{|\varepsilon_L| + |\varepsilon_C|}{2 \cdot s}\right)$$

On the other hand, a self-locking effect of the tapered first and second seat surfaces 14a, 14b is not desirable.

The following should apply to the opening angle α in order to prevent a self-locking effect:

$$\alpha > \arctan \mu_H,$$

wherein $\mu_H$ is the static friction coefficient between the first and second seat surface 14a, 14b.

By taking these conditions into account, the opening angle α should be around between 5° and 15°, more preferably around 10°.

Figure 2:
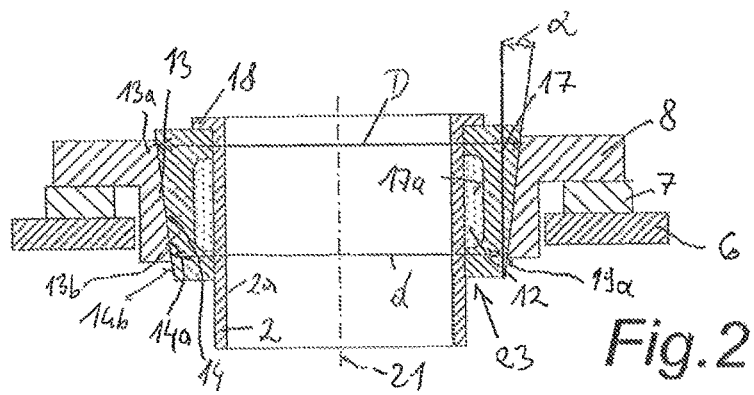
FIG. 2 shows the liner carrier and the cylinder liner of the first embodiment shown in FIG. 1 in a schematic longitudinal sectional view.

In the first embodiment shown in FIG. 1 and FIG. 2, the cylinder liner 2 is arranged in a sleeve-like liner frame 17 which surrounds the cylinder liner 2. The cylinder liner 2 is formed in a cylindrical manner. The inner surface of the liner frame 17 is formed in a tubular manner and accommodates the cylinder liner 2. The tapered second seat surface 14b is formed by the outer jacket 19a of the liner frame 17, which is formed in a tapered manner corresponding to the first seat surface 14a. The liner frame 17 need not extend in the axial direction over the full length of the cylinder liner 2. It is sufficient if the cylinder liner 2 is supported by the liner frame 17 in an upper part facing the cylinder head 9, e.g. the upper half. The cooling jacket 12 is arranged between the cylinder liner 2 and the liner frame 17. In the illustrated first embodiment, the cooling jacket 12 is formed by an annular recess 17a of the liner frame 17. It is also possible to arrange the cooling jacket 12 in the cylinder liner 2 or partly in the cylinder liner 2 and partly in the liner frame 17. The liner frame 17 is connected in a liquid-tight manner to the cylinder liner 2, e.g. pressed onto said liner. It is also possible to provide soldered, welded and/or glued connections.

Figure 3:
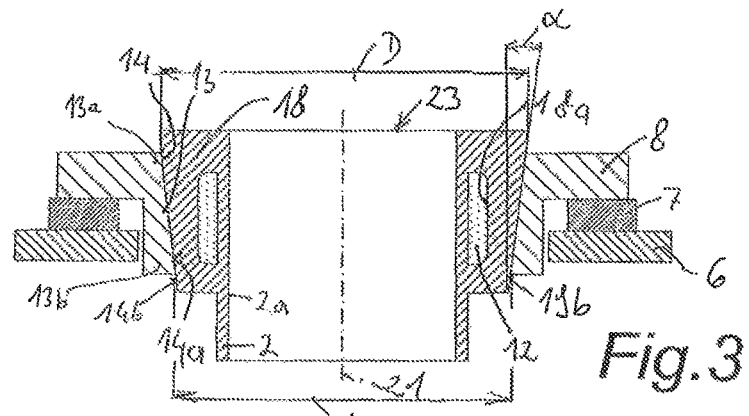
FIG. 3 shows the liner carrier and the cylinder liner in a second embodiment in a schematic longitudinal sectional view.
Figure 4:
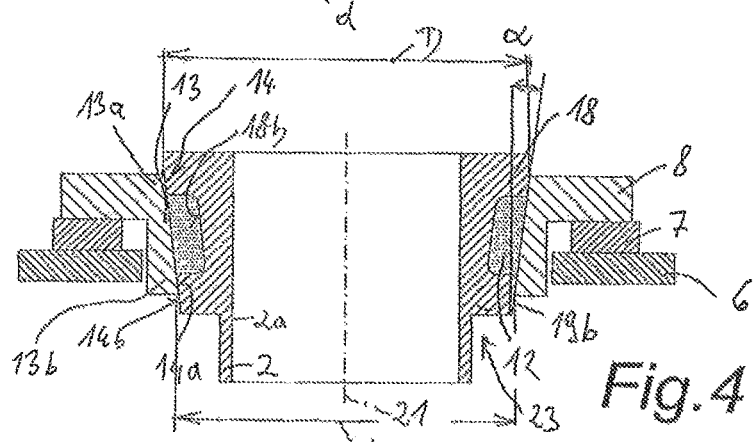
FIG. 4 shows the liner carrier and the cylinder liner in a third embodiment in a schematic longitudinal sectional view.
Figure 5:
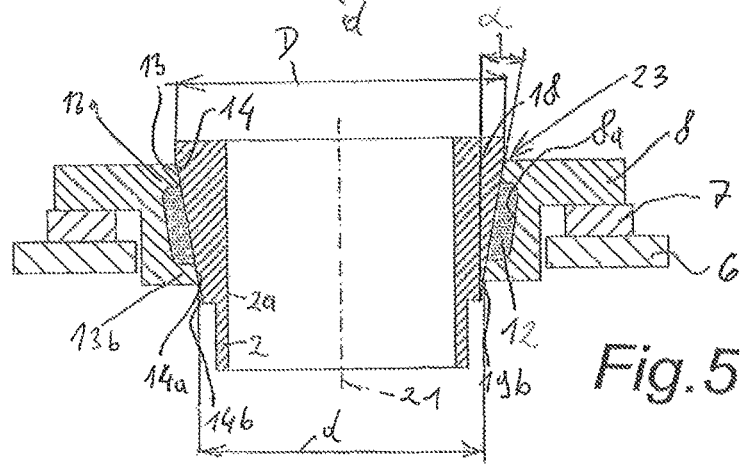
FIG. 5 shows the liner carrier and the cylinder liner in a fourth embodiment in a schematic longitudinal sectional view.

FIGS. 3 to 5 show embodiments without a separate liner frame, which only differ from each other by the position of the coolant jacket 12. The second seat surface 14b of the tapered seat 14 is formed in each of these embodiments by the outer jacket surface 19b of the liner flange 18 of the cylinder liner 2.

In the case of the second and third embodiments shown in FIG. 3 and FIG. 4, the cooling jacket 12 is respectively arranged in the liner flange 18 of the cylinder liner 2.

In the second embodiment shown in FIG. 3, the coolant jacket 12 is formed by an annular cavity 18a within the liner flange 18. Said cavity 18a can be formed by a lost core for example. Separate sealing of the coolant jacket 12 is not necessary. The second embodiment thus represents a further development of the first embodiment with few parts.

Conversely, the coolant jacket 12 is formed in the third embodiment of the invention shown in FIG. 4 by a groove-shaped annular recess 18b in the outer jacket of the liner flange 18.

FIG. 5 shows a further embodiment, in which the coolant jacket 12 is formed by an annular recess 8a in the receiving region 13 of the liner carrier 8.

In the case of a respectively fine machining of the first and second seat surfaces 14a, 14b of the tapered seat 14, the coolant jacket 12 is automatically sealed during insertion of the cylinder liner 2 into the tapered seat 14 in the third and fourth embodiments shown in FIG. 4 and FIG. 5, without requiring any further sealing elements.

Each of the illustrated embodiments comes with the advantage that cylinder liners 2 can be exchanged very easily for tests of different liners, without having to release the retaining screws 24 or screws 20 which connect the liner carrier 8 and the sensor carrier 6. This avoids laborious calibrating work.

For the purpose of exchanging the cylinder liner 2, it is extracted, in the first embodiment, plus the liner frame 17, from the liner carrier 8 and replaced by a different cylinder liner 2. The new cylinder liner 2 centres automatically in the tapered seat 14. The self-centring tapered seat 14 allows simple separation of the cylinder liner 2 from the liner carrier 8.

The invention claimed is:

1. A device for measuring friction on a cylinder-piston arrangement that includes a reciprocating piston arranged in a cylinder liner of a liner unit, wherein said liner unit comprises the cylinder liner which is decoupled from a cylinder head, and a liner frame accommodating the cylinder liner, and said liner unit is arranged in a liner carrier which is connected to a sensor carrier and which has a receiving region for the cylinder liner, said receiving region being rotationally symmetrical and concentric to an axis of the cylinder, wherein the liner unit is mounted in the liner carrier via a tapered seat, wherein at least one tapered inner jacket surface of the receiving region forms a first seat surface and a tapered outer jacket surface of the liner unit that is shaped in a manner reciprocal to the first seat surface forms a second seat surface of the tapered seat for receiving and centering the cylinder liner, wherein the second seat surface is formed by the liner frame, and including a cooling jacket for the cylinder liner, the coolant jacket being formed between the liner frame and the cylinder.

2. The device according to claim 1, wherein the cylinder liner and the liner frame are rigidly connected to each other.

3. The device according to claim 1, wherein the liner frame is formed in a sleeve-like manner.

4. The device according to claim 1, wherein the cylinder liner and the liner frame are connected to each other by pressing.

5. The device according to claim 1, wherein the first seat surface has an opening angle in relation to the cylinder axis which opens in a direction of the cylinder head.

6. The device according to claim 5, wherein the opening angle is between 5° and 15°.

7. The device according to claim 5, wherein the opening angle is about 10°.

8. The device according to claim 1, wherein at least one of the cylinder liner and the liner frame is fastened to the liner carrier via a retaining ring.

9. A device for measuring friction on a cylinder-piston arrangement that includes a reciprocating piston arranged in a cylinder liner of a liner unit, wherein said liner unit comprises the cylinder liner which is decoupled from a cylinder head and a liner frame accommodating the cylinder liner, wherein said liner unit is arranged in a liner carrier which is connected to a sensor carrier and which has a receiving region for the cylinder liner, said receiving region being rotationally symmetrical and concentric to an axis of the cylinder, wherein the liner unit is mounted in the liner carrier via a tapered seat, wherein at least one tapered inner jacket surface of the receiving region forms at first seat surface and a tapered outer jacket surface of the liner unit that is shaped in a manner reciprocal to the first seat surface forms a second seat surface of the tapered seat for receiving and centering the cylinder liner, wherein the second seat surface is formed by the liner frame, including means providing a cooling jacket for the cylinder liner, and wherein the coolant jacket is moulded at least partly into the liner frame.

* * * * *